United States Patent
Khajehim (10) Patent No.: US 11,867,785 B2
(45) Date of Patent: Jan. 9, 2024

(54) **DUAL GRADIENT ECHO AND SPIN ECHO MAGNETIC RESONANCE FINGERPRINTING FOR SIMULTANEOUS ESTIMATION OF T1, T2, AND T2* WITH INTEGRATED B1 CORRECTION**

(71) Applicant: Baycrest Centre for Geriatric Care, Toronto (CA)

(72) Inventor: Mahdi Khajehim, Toronto (CA)

(73) Assignee: Baycrest Centre for Geriatric Care, Toronto (CA)

( * ) Notice: Subject to any disclaimer, the term of this patent is extended or adjusted under 35 U.S.C. 154(b) by 0 days.

(21) Appl. No.: 17/603,188

(22) PCT Filed: Apr. 9, 2020

(86) PCT No.: PCT/CA2020/050481
§ 371 (c)(1),
(2) Date: Oct. 12, 2021

(87) PCT Pub. No.: WO2020/206553
PCT Pub. Date: Oct. 15, 2020

(65) Prior Publication Data
US 2022/0206095 A1  Jun. 30, 2022

Related U.S. Application Data

(60) Provisional application No. 62/833,131, filed on Apr. 12, 2019.

(51) Int. Cl.
*G01R 33/50* (2006.01)
*A61B 5/055* (2006.01)
*G01R 33/32* (2006.01)
*G01R 33/385* (2006.01)
*G06N 3/08* (2023.01)

(52) U.S. Cl.
CPC .............. *G01R 33/50* (2013.01); *A61B 5/055* (2013.01); *G01R 33/32* (2013.01); *G01R 33/385* (2013.01); *G06N 3/08* (2013.01)

(58) Field of Classification Search
CPC ...... G01R 33/50; G01R 33/32; G01R 33/385; A61B 5/055; G06N 3/08
See application file for complete search history.

(56) References Cited

U.S. PATENT DOCUMENTS

2018/0231626 A1* 8/2018 Gulani ............... G01R 33/5602
2019/0353737 A1* 11/2019 Ma ..................... G01R 33/5608

* cited by examiner

*Primary Examiner* — G. M. A Hyder
(74) *Attorney, Agent, or Firm* — Quarles & Brady LLP (57) ABSTRACT

Magnetic resonance fingerprinting ("MRF") techniques in which T1, T2, and T2* are simultaneously quantified using a combined gradient echo and spin echo acquisition with integrated B1 correction are described. The values for T2 and T2* can be estimated separately, but using the same underlying dictionary. This approach enables a smaller dictionary size that is easily manageable, and also reduced error propagation. Moreover, by using echo planar imaging ("EPI") readouts, the raw MRF images will have higher signal-to-noise ratio ("SNR") relative images acquired using spiral-based MRF techniques. The EPI-based images are also relatively free of artifacts. Together, these advantages lead to the need for far fewer frames, thereby enabling much faster acquisitions. Moreover, offline reconstruction is not needed, allowing for a more straightforward implementation of MRF.

14 Claims, 6 Drawing Sheets

DUAL GRADIENT ECHO AND SPIN ECHO MAGNETIC RESONANCE FINGERPRINTING FOR SIMULTANEOUS ESTIMATION OF T1, T2, AND T2* WITH INTEGRATED B1 CORRECTION

CROSS-REFERENCE TO RELATED APPLICATIONS

The present application represents the U.S. national stage entry of International Patent Application No. PCT/CA2020/050481, filed on Apr. 9, 2020, and claims the benefit of U.S. Provisional Patent Application Ser. No. 62/833,131, filed on Apr. 12, 2019, and entitled "DUAL GRADIENT ECHO AND SPIN ECHO MAGNETIC RESONANCE FINGERPRINTING FOR SIMULTANEOUS ESTIMATION OF T1, T2, AND T2* WITH INTEGRATED B1 CORRECTION," the contents of each of which are herein incorporated by reference in their entirety.

BACKGROUND

Quantitative magnetic resonance imaging ("qMRI") typically refers to the quantitative mapping of tissue parameters such as T1, T2, and proton density ("PD") values. Compared to the currently dominant qualitative T1-weighted, T2-weighted, and PD-weighted techniques, qMRI provides improved accuracy and sensitivity for detecting and monitoring different neurological and other pathologies, including stroke, Alzheimer's disease, and brain or other tumors. Moreover, qMRI findings are relatively immune to image artifacts. Consequently, the development of qMRI approaches is important in clinical applications. However, conventional qMRI methods are limited by very long acquisition times that are considered unfeasible in routine clinical practice. As a result, a need exists for imaging approaches that can estimate multiple tissue parameters in a fast and robust way.

Magnetic resonance fingerprinting ("MRF") is a quantitative imaging method that can give estimates of the above qMRI parameters as well as field-uniformity related parameters at the same time. In MRF, sequence parameters are varied dynamically in a pseudo-random pattern, and then the acquired signal is compared with a pre-calculated dictionary based on the Bloch equation using a pattern matching algorithm. Each dictionary entry corresponds to a set of predetermined qMRI parameters, and the matching dictionary entry provides simultaneous estimates of these parameters. So far, MRF has been mostly limited to quantification of T1 and T2. Most commonly, a spiral readout with a large undersampling factor is used to speed up image acquisition. To randomize undersampling artifacts, rotating undersampled spiral readouts are typically used. Moreover, short echo times are used to make the approach less sensitive to off-resonance effects.

In addition to T1 and T2, there have been few recent attempts to include T2* in the MRF framework due to proven clinical value. Despite initial evidence of feasibility, attempts at including T2* have been limited by longer necessary TEs, which make designing undersampled spiral pattern and accurate parameter estimation more challenging; needing extremely large dictionaries, which makes the whole approach hard to deal with in practice; and using a T2 and T2* estimation that is coupled in a way such that errors in the T2 estimation can propagate into T2* quantification. Furthermore, all of these approaches use undersampled spiral readout with off-line image reconstruction that comes with its own challenges in terms of scan time, ease of implementation, and accessibility.

Very recently, a non-spiral MRF approach for T2* quantification has been suggested using an echo-planar (EPI) readout. A gradient-spoiled gradient-echo (GE) sequence with varying TE, TR, and FA was used for T1 and T2* quantification in this example. Despite promising results, this approach is unable to provide estimates of tissue T2 due to the GE based implementation.

SUMMARY OF THE DISCLOSURE

The present disclosure addresses the aforementioned drawbacks by providing a method for generating T1, T2, and T2* parameter maps from data acquired with a magnetic resonance imaging (MRI) system. Magnetic resonance data are acquired from a subject by operating an MRI system to acquire the magnetic resonance data in a series of variable sequence blocks to cause one or more resonant species in the subject to simultaneously produce individual magnetic resonance signals. At least one member of the series of variable sequence blocks differs from at least one other member of the series of variable sequence blocks in at least one two sequence block parameters. The series of sequence blocks includes a first segment comprising a first plurality of variable sequence blocks in which data are acquired by sampling gradient echoes and a second segment comprising a second plurality of variable sequence blocks in which data are acquired by sampling spin echoes. As such, the magnetic resonance data comprises first magnetic resonance data acquired during the first segment and second magnetic resonance data acquired during the second segment. A first series of parameter maps is generated by estimating T1, T2*, and B1 values with a computer system by comparing the first data to a dictionary of signal evolutions. This first series of parameter maps depicts spatial distributions of T1, T2*, and B1 values. A second series of parameter maps is then generated by estimating T2 values with the computer system by comparing the second data to the dictionary of signal evolutions while constraining T1 values with those estimated from the first data. This second series of parameter maps depicts spatial distributions of T2 values.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for implementing magnetic resonance fingerprinting ("MRF") to simultaneously quantify T1, T2, and T2*, using a combined gradient echo and spin echo acquisition with integrated B1 correction. The values for T2 and T2* can be estimated separately, but using the same underlying dictionary. This approach enables a smaller dictionary size that is easily manageable, and also reduces error propagation. Moreover, by using echo planar imaging ("EPI") readouts, the raw MRF images will have visibly higher signal-to-noise ratio ("SNR") relative to images acquired using spiral-based MRF techniques. The EPI-based images are also relatively free of artifacts. Together, these advantages lead to the need for far fewer frames, thereby enabling much faster acquisitions. Moreover, offline reconstruction is not needed, allowing for a more straightforward implementation of MRF.

MRF is a technique that facilitates mapping of tissue or other material properties based on random or pseudorandom measurements of the subject or object being imaged. In particular, MRF can be conceptualized as employing a series of varied "sequence blocks" that simultaneously produce different signal evolutions in different "resonant species" to which radio frequency ("RF") energy is applied. The term "resonant species," as used herein, refers to a material, such as water, fat, bone, muscle, soft tissue, and the like, that can be made to resonate using NMR. By way of illustration, when RF energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The random or pseudorandom measurements obtained in MRF techniques can be achieved by varying the acquisition parameters from one repetition time ("TR") period to the next, which creates a time series of signals with varying contrast Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, MRF processes can be designed to map any of a wide variety of parameters. Examples of such parameters that can be mapped may include, but are not limited to, longitudinal relaxation time, $T_1$; transverse relaxation time, $T_2$; apparent transverse relaxation time, $T_2^*$ main or static magnetic field map, $B_0$; proton density, $\rho$; and RF field strength, $B_1$. As noted, it is an aspect of the present disclosure to provide an MRF framework in which T1, T2, T2*, and B1 can be estimated from data acquired using a single series of variable sequence blocks, and using the same underlying dictionary.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \qquad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_1(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1,T_2,D)$, may also include additional terms, $E_i(T_1, T_2, D, \ldots)$ or may include fewer terms, such as by not including the diffusion relaxation, as $E_i(T_1, T_2)$ or $E_i(T_1, T_2, \ldots)$. Also, the summation on "j" could be replace by a product on "j".

The dictionary may store signals described by, $$S_i = R_i E_i(S_{i-1}) \qquad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

As will be described, the present disclosure provides an MRF framework for quantifying T1, T2, and T2* using a combined gradient echo and spin echo acquisition with integrated B1 correction. In general, magnetic resonance data are acquired from a subject using an MRI system that is operated to implement a series of variable sequence blocks to cause one or more resonant species in the subject to simultaneously produce individual magnetic resonance signals. At least one member of this series of variable sequence blocks will differ from at least one other member of the series of variable sequence blocks in at least one sequence block parameter (e.g., TE, TR, FA).

The series of sequence blocks includes a first segment composed of a first plurality of variable sequence blocks in which data are acquired by sampling gradient echoes. The series of sequence blocks also includes a second segment composed of a second plurality of variable sequence blocks in which data are acquired by sampling spin echoes. In this way, the acquired magnetic resonance data includes first magnetic resonance data acquired during the first segment and second magnetic resonance data acquired during the second segment. Preferably, the data are acquired in each sequence block using an EPI readout.

Using an EPI readout, for instance, enables fast image acquisition with readily available approaches for correcting gradient delays, imperfections, and nonlinearities. In addition, due to the absence of undersampling artifacts when using an EPI readout compared to a spiral readout, far fewer imaging volumes are needed for accurate parameter estimation, again relative to spiral or radial readouts. This reduced number of imaging volumes leads to faster dictionary generation, lower storage requirements, and faster dictionary matching. For example, the dictionary size can be several times smaller than one based on spiral readouts. The higher image quality attainable using EPI readouts also lends itself to the use of accelerated dictionary-matching and more accurate partial volume estimation, as the image artifacts present in undersampled spirals is one of the major challenges in these aspects.

A first series of parameter maps is generated by estimating T1, T2* and B1 values with a computer system by comparing the first data to a dictionary of signal evolutions. This first series of parameter maps, therefore, depicts spatial distributions of T1, T2* and B1 values. A second series of parameter maps is then generated by estimating T2 values with the computer system by comparing the second data to the dictionary of signal evolutions while constraining the dictionary matching using the T1 values estimated from the first data. This second series of parameter maps depicts spatial distributions of T2 values.

Thus, in the systems and methods described in the present disclosure, data can be acquired using a spin echo ("SE") segment, such as a SE-EPI segment, that can be added at the end of a gradient echo ("GE") segment, such as a GE-EPI sequence. This implementation has several advantages. First, as T1 and B1 can both be quantified in the GE segment and fed into the dictionary-matching process for the SE segment, the SE segment requires far fewer volumes than the GE segment. For instance, the SE segment can contain less than one-third of the volumes in the GE segment. Also, assuming T2* decay is mono-exponential (like T2), the same dictionary can be utilized to get estimates of both T2 and T2* without adding another dimension to the dictionary. As another advantage, the T2 and T2* estimation can be performed from data acquired in separate (GE and SE) halves of the sequence, such that error in estimating one does not affect the other.

Figure 1A:
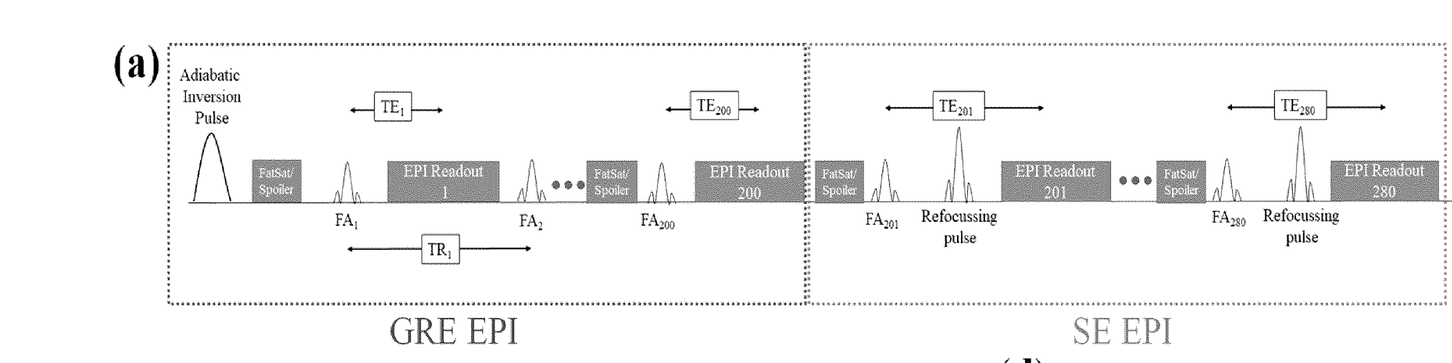
FIGS. 1A-1D show an example of a series of variable sequence blocks (FIG. 1A) containing a first segment of sequence blocks that acquire data from gradient echoes using an echo planar imaging ("EPI") readout and a second segment of sequence blocks that acquire data from spin echoes using an EPI readout. The change in flip angle (FIG. 1B), echo time (FIG. 1C), and repetition time (FIG. 1D) over the series of sequence blocks are also shown.
Figure 1B:
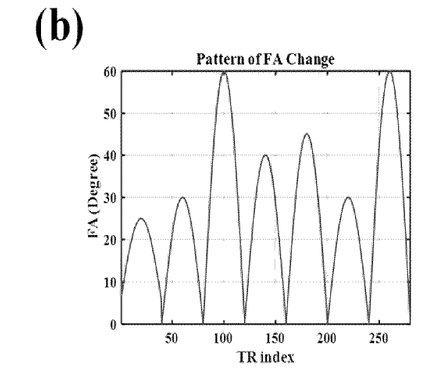
Figure 1C:
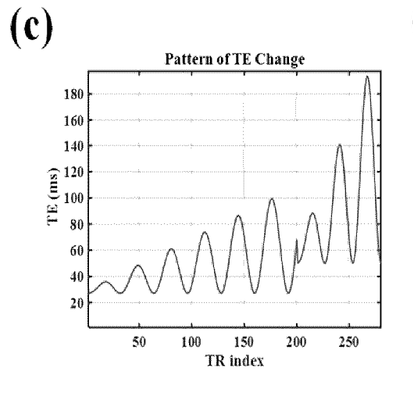
Figure 1D:
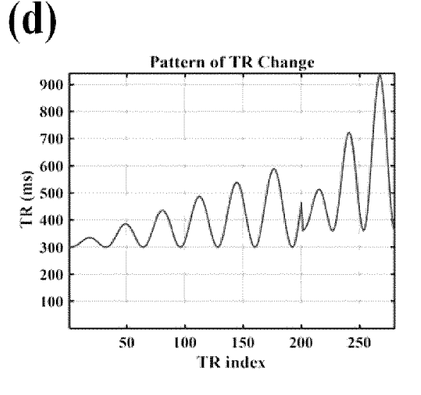

A schematic view of an example series of variable sequence blocks is shown in FIG. 1A. In this example implementation, data are acquired in each sequence block using an EPI readout. The first segment of the series of variable sequence blocks acquires data by sampling gradient echoes (e.g., using GE-EPI sequence blocks), and the second segment acquires data by sampling spin echo (e.g., using SE-EPI sequence blocks). An example pattern of flip angle ("FA") changes over the series of variable sequence blocks is shown in FIG. 1B. An example pattern of echo time ("TE") changes over the series of variable sequence blocks is shown in FIG. 1C. An example pattern of repetition time ("TR") change over the series of variable sequence blocks is shown in FIG. 1D.

In some examples, the GE-EPI sequence blocks can contain one or more hyperbolic secant adiabatic inversion pulses, which may be position at the beginning of a given sequence block or elsewhere during a given sequence block. In the example shown in FIGS. 1A-1D, the GE-EPI segment includes a semi-random pattern of FA change with five half periods of a sinusoid, with FAs ranging overall from 0 to 60 degrees. Similarly, in the example shown in FIGS. 1A-1D, TEs varied between 25-100 ms while TR was the shortest possible for each TE (range 65-140 ms). In addition to fat saturation, both gradient and RF spoiling can be implemented while using crusher gradients before the fat saturation module as a gradient spoiler for water (in all x, y, and z directions).

In the example shown in FIGS. 1A-1D, after 200 GE-EPI frames, the series of variable sequence blocks transitions into SE-EPI for another 80 frames. In each sequence block in this second segment, a slice-selective refocusing RF pulse is applied before the EPI readout. Crusher gradients can be added in all three directions to spoil the free induction decay ("FID") signal that may result from non-ideal refocusing. In the SE-EPI segment shown in FIGS. 1A-1D, the TE range is 50-190 ms. To counteract the partial saturation of the longitudinal magnetization due to refocusing pulse and to ensure sufficient level of longitudinal magnetization, a recovery time (e.g., a 300 ms recovery time) may be added after each EPI readout in the SE-EPI segment. When using a multislice acquisition, this recovery time may not be needed.

Other sequence parameters common to both the GE-EPI and SE-EPI segments shown in FIGS. 1A-1D are: matrix size=128×128, FOV=220×220 mm, voxel size=1.7×1.7×2 mm, GRAPPA factor=2, number of reference lines=62, no partial Fourier, BW/Pixel=1562 Hz, Total acquisition time per slice is approximately 44 s.

Each voxel is represented by one isochromat. In one non-limiting example, the dictionary used for estimating the quantitative parameters from the data acquired using the series of variable sequence blocks can be generated using the discrete form of the Bloch equations. RF pulses can be assumed to be instantaneous, and the RF-slice profile can be ignored for simplicity while B1 inhomogeneity can be explicitly included in the model.

As noted above, a two-step dictionary-matching technique is implemented. In such an approach, the transverse signal decay in the GE segment is assumed to represent $T2^*$ while the transverse signal decay in the SE segment is assumed to represent T2. The GE data are used to obtain estimates of T1, $T2^*$, and B1, whereas the SE data are used to match for T2, after adopting the T1 and B1 values from the GE-matching stage. In this way, the second stage of the dictionary matching is constrained by the first stage. For instance, the GE-EPI portion of the data is used to estimate the T1 and $T2^*$ (and B1) values, ignoring T2 effects. In the second stage, it is then assumed that the T1 is the same as the T1 from the SE-EPI portion of the data, and then match for T2. As a result, the same dictionary can be used in the first stage and the second stage, but in the second stage matching $T2^*$ is treated as T2.

In one example dictionary, the simulated range of T1 was 50:25:2500 ms the $T2/T2^*$ range was 10:5:250 ms, and relative B1 was assumed to vary between 0.5 and 1.5 with a step size of 0.1. Overall, this example dictionary has approximately 48,000 entries and required 100 MB of storage.

Pattern matching can be implemented using the magnitude of the magnetic resonance signal using a maximum dot product approach. Other pattern matching techniques can also be implemented. In some implementations, pattern matching can be achieved by inputting images reconstructed from the acquired magnetic resonance data to a suitably trained neural network, generating output as one or more parameter maps.

To estimate T2 with EPI readouts, the reversible part of $T2^*$ decay should be minimized. It may be possible to use a very short TE along with an optimized pattern of TR/FA change to get estimates of T2 with an EPI readout. It may be advantageous to not fully ignore off-resonance effects, even with such a short TE. In some instances, a T2 preparation using a refocusing pulse can be used to compensate for the off-resonance effects. Here, a more pure T2 contrast is achieved using an additional refocusing pulse (i.e., SE-EPI) to compensate for the off-resonance effects. With the TR range involved, this could lead to saturation of the longitudinal magnetization. In the examples described above, a recovery time (e.g., 300 ms) was added after each readout to let the signal recover. It is contemplated that increasing this recovery time may also increase the baseline signal to the point that an even lower number of image volumes may be required for accurate parameter estimation. In addition, this wait time can potentially be leveraged to acquire more slices.

Figure 2:
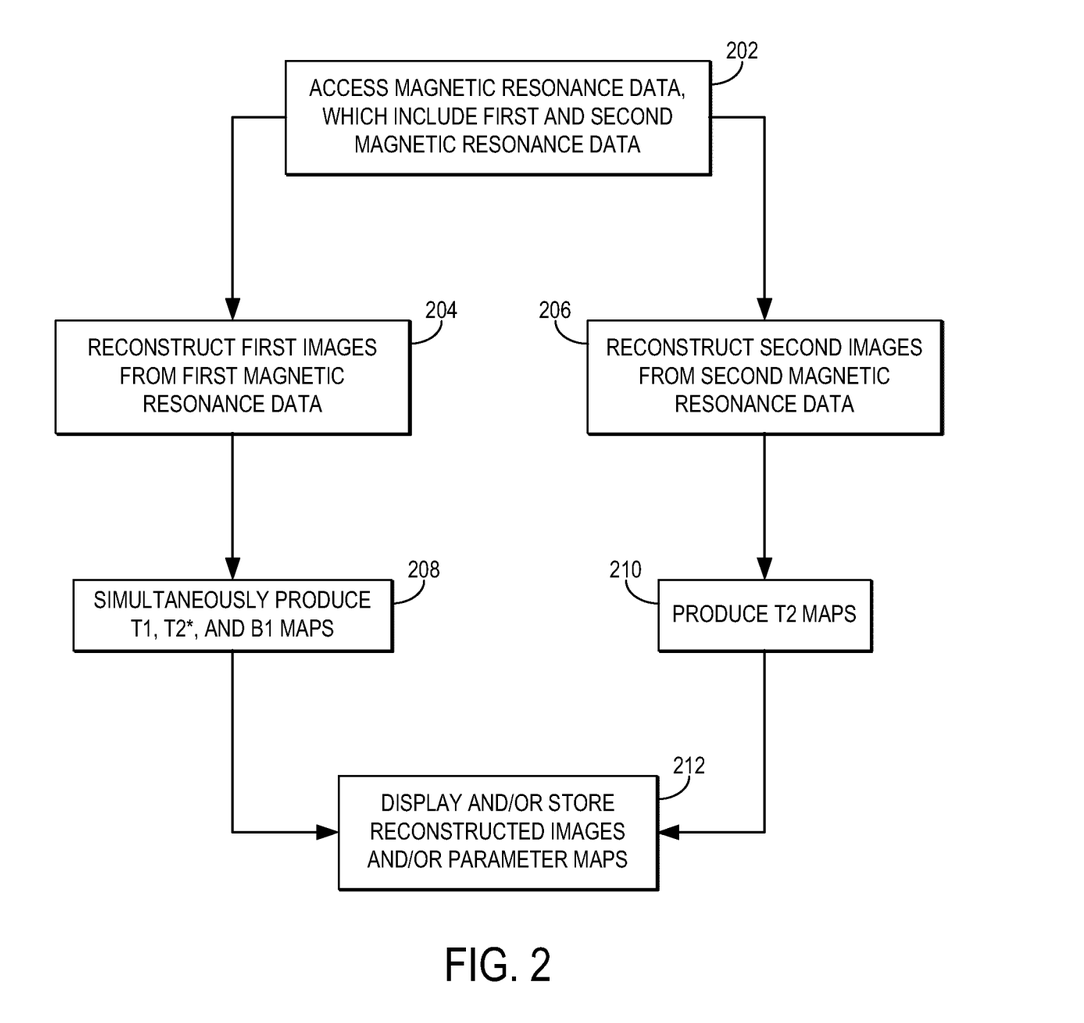
FIG. 2 is a flowchart setting forth the steps of an example method for generating T1, T2, T2*, and/or B1 maps from magnetic resonance data acquired using GE-EPI and SE-EPI data using magnetic resonance fingerprinting techniques.

Referring now to FIG. 2, a flowchart is illustrated as setting forth the steps of an example method for using magnetic resonance fingerprinting techniques to generate T1, T2, $T2^*$, and/or B1 maps from magnetic resonance data acquired using GE-EPI and SE-EPI data.

The method includes accessing magnetic resonance data with a computer system, as indicated at step 202. Accessing the magnetic resonance data may include retrieving such data from a memory or other suitable data storage device or medium. Alternatively, accessing the magnetic resonance data may include acquiring such data with an MRI system and transferring or otherwise communicating the data to the computer system, which may be a part of the MRI system.

In general, the magnetic resonance data are acquired from a subject using an MRI system that is operated to implement a series of variable sequence blocks to cause one or more resonant species in the subject to simultaneously produce individual magnetic resonance signals. At least one member of this series of variable sequence blocks will differ from at least one other member of the series of variable sequence blocks in at least one sequence block parameter (e.g., TE, TR, FA).

The series of sequence blocks includes a first segment composed of a first plurality of variable sequence blocks in which data are acquired by sampling gradient echoes. The series of sequence blocks also includes a second segment composed of a second plurality of variable sequence blocks in which data are acquired by sampling spin echoes. In this way, the acquired magnetic resonance data includes first magnetic resonance data acquired during the first segment and second magnetic resonance data acquired during the second segment. Preferably, the data are acquired in each sequence block using an EPI readout.

Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, and amount of gradient spoiling.

Depending upon the imaging or clinical need, two, three, four, or more parameters may vary between sequence blocks. The number of parameters varied between sequence blocks may itself vary. For example, a first sequence block may differ from a second sequence block in five parameters, the second sequence block may differ from a third sequence block in seven parameters, the third sequence block may differ from a fourth sequence block in two parameters, and so on. One skilled in the art will appreciate that there are a very-large number of series of sequence blocks that can be created by varying this large number of parameters. A series of sequence blocks can be crafted so that the series have different amounts (e.g., 1%, 2%, 5%, 10%, 50%, 99%, 100%) of unique sequence blocks as defined by their varied parameters. A series of sequence blocks may include more than ten, more than one hundred, more than one thousand, more than ten thousand, and more than one hundred thousand sequence blocks. In one example, the only difference between consecutive sequence blocks may be the number or parameters of excitation pulses.

Regardless of the particular imaging parameters that are varied or the number or type of sequence blocks, the RF energy applied during a sequence block is configured to cause different individual resonant species to simultaneously produce individual magnetic resonance signals. Unlike conventional imaging techniques, in an MRF pulse sequence, at least one member of the series of variable sequence blocks will differ from at least one other member of the series of variable sequence blocks in at least N sequence block parameters, where N is an integer greater than one. One skilled in the art will appreciate that the signal content of a signal evolution may vary directly with N. Thus, as more parameters are varied, a potentially richer signal is retrieved. Conventionally, a signal that depends on a single parameter is desired and required to facilitate imaging. Here, acquiring signals with greater information content facilitates producing more distinct, and thus more matchable, signal evolutions.

In some implementations, the magnetic resonance data can be acquired using a simultaneous multislice ("SMS") acquisition, in which data are simultaneously acquired from two or more different slices. As one example, a blipped-CAIPI type acquisition can be used. For instance, when using blipped-CAIPI the RF pulses in the pulse sequence shown in FIG. 1A can be replaced with their multiband SMS versions (except for the initial inversion pulse, which is non-selective).

As a non-limiting example, magnetic resonance data can be acquired using the sequence(s) schematically shown in FIG. 1A. As described above, both GE-EPI and SE-EPI data are acquired in the same acquisition. This dual-stage design offers a number of advantages. As one advantage, because T1 and B1 can both be quantified in the GE-EPI segment and then fed into the dictionary-matching process for the SE-EPI segment, it has been found that even as few as 80 volumes (less than half the number of volumes in the GE segment) can be enough for accurate T2 estimation. As another advantage, because T2 and T2* estimations can be performed from data acquired in separate (GE and SE) segments of the sequence, errors in one estimate will not affect the other. As still another advantage, the dual GE-EPI and SE-EPI sequence minimizes chances for movement and changes in shimming, in subject positioning, and/or in scanner scaling factor.

Referring still to FIG. 2, the method continues by reconstructing first images from the first magnetic resonance data, as indicated at step 204, and second images from the second magnetic resonance data, as indicated at step 206. When an EPI sequence that sampled k-space along a Cartesian trajectory is used to acquire the data, reconstruction can be achieved using a conventional Fourier transform-based reconstruction, which introduces another reduction in the computational burden compared to conventional MRF applications that require complex reconstruction techniques to reconstruct images from data acquired using non-Cartesian trajectories.

As described above, a two-step dictionary-matching approach can be used to generate parameter maps. For example, the GE data (e.g., the first magnetic resonance data or corresponding first images) are used to obtain estimates of T1 and T2* (and optionally B1), whereas in the second step, the SE data (e.g., the second magnetic resonance data or second images) are used to only match for T2

A first series of parameter maps is thus generated based on a comparison of the first images with one or more pre-computed dictionaries, as indicated at step 208. In some implementations, the comparison can be made using pattern matching or other such techniques. For example, the comparison can be based on a maximum dot product approach. In some other implementations, the comparison can be made by inputting the reconstructed imaged to a trained neural network, generating output as the estimated parameter maps. As described above, it is an advantage of the methods described in the present disclosure to simultaneously estimate T1, T2* and B1 by comparing the first images to a dictionary of signal evolutions. This first series of parameter maps, therefore, depicts spatial distributions of T1, T2* and B1 values.

A second series of parameter maps is then generated based on a comparison of the second images with one or more pre-computed dictionaries, as indicated at step 210. In some implementations, the comparison can be made using pattern matching or other such techniques. For example, the comparison can be based on a maximum dot product approach. In some other implementations, the comparison can be made by inputting the reconstructed images to a trained neural network, generating output as the estimated parameter maps. When using a neural network, the T1 (and optionally B1) parameter maps can be additionally input to the trained neural network with the second images in order to generate output as the T2 parameter maps. As described above, T2 values can be estimated by comparing the second images to the same dictionary of signal evolutions used for generating the first series of parameter maps. This second series of parameter maps, therefore, depicts spatial distributions of T2 values.

The reconstructed first and second images and the generated first and second series of parameter maps can then be displayed to a user or stored for later use, as indicated at step 212.

As noted above, in some instances, parameter maps can be generated by inputting the respective images to a suitably trained neural network. Using a trained neural network allows for a reduction in the dictionary size. The use of a trained neural network also allows for parameter estimation that is orders of magnitude faster than conventional dictionary matching. For instance, it may take only a few minutes to compute whole brain T1, T2, and T2* maps.

Figure 3:
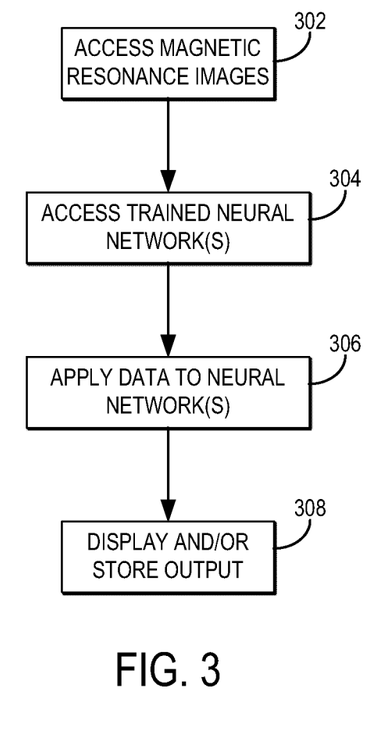
FIG. 3 is a flowchart setting forth the steps of an example method for generating parameter maps by inputting magnetic resonance images to a neural network that has been trained in part on a dictionary of signal evolutions as training data.

Referring now to FIG. 3, a flowchart is illustrated as setting forth the steps of an example method for generating a series of parameter maps using a suitably trained neural network or other machine learning algorithm.

The method includes accessing magnetic resonance images with a computer system, as indicated at step 302. Accessing the magnetic resonance images may include retrieving such data from a memory or other suitable data storage device or medium. Alternatively, accessing the magnetic resonance images may include acquiring such data with an MRI system as described above, and transferring or otherwise communicating the data to the computer system, which may be a part of the MRI system. The magnetic resonance images can, in some instances, also include parameter maps, such as T1 parameter maps and/or B1 parameter maps.

One or more trained neural networks (or other suitable machine learning algorithms) are then accessed with the computer system, as indicated at step 304. Accessing the trained neural network(s) may include accessing network parameters (e.g., weights, biases, or both) that have been optimized or otherwise estimated by training the neural network on training data. In some instances, retrieving the neural network(s) can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data in order to generate parameter maps. In some instances, more than one trained neural network may be accessed. For example, a first neural network may have been trained on first training data to generate a first series of parameter maps (e.g., T1, T2*, and/or B1 maps) and a second neural network may have been trained on second training data to generate a second series of parameter maps (e.g., T2 maps).

The magnetic resonance images are then input to the one or more trained neural networks, generating output as parameter maps, as indicated at step 306. For example, the first images can be input to a first trained neural network, generating output as T1, T2*, and/or B1 maps. The second images can then be input to a second neural network, generating output as T2 maps. Additionally, the T1 and/or B1 maps output from the first neural network can also be input to the second neural network together with the second images in order to generate output as the T2 maps.

The parameter maps generated by inputting the magnetic resonance images to the trained neural network(s) can then be displayed to a user, stored for later use or further processing, or both, as indicated at step 308.

Figure 4:
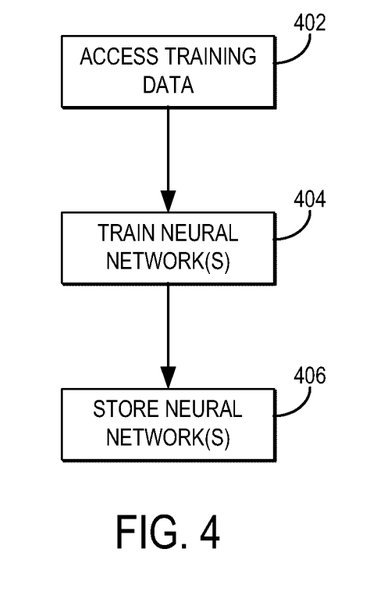
FIG. 4 is a flowchart setting forth the steps of an example method for training a neural network based in part on a dictionary of signal evolutions as training data.

Referring now to FIG. 4, a flowchart is illustrated as setting forth the steps of an example method for training one or more neural networks (or other suitable machine learning algorithms) on training data, such that the one or more neural networks are trained to receive input as magnetic resonance images and/or parameter maps in order to generate output as parameter maps, such as T1 maps, T2* maps, B1 maps, and/or T2 maps.

In general, the neural network(s) can implement any number of different neural network architectures. For instance, the neural network(s) could implement a convolutional neural network, a residual neural network, a deep neural network, or so on. Alternatively, the neural network(s) could be replaced with other suitable machine learning algorithms, such as those based on supervised learning, unsupervised learning, deep learning, ensemble learning, dimensionality reduction, and so on.

The method includes accessing training data with a computer system, as indicated at step 402. Accessing the training data may include retrieving such data from a memory or other suitable data storage device or medium. Alternatively, accessing the training data may include acquiring such data with an MRI system and transferring or otherwise communicating the data to the computer system, which may be a part of the MRI system. In some implementations, the training data can include simulated data, such as simulated signal evolution data.

Additionally or alternatively, the method can include assembling training data from magnetic resonance signal evolutions, whether in acquired magnetic resonance data or simulated magnetic resonance data, using a computer system. This step may include assembling the magnetic resonance signal evolutions into an appropriate data structure on which the neural network can be trained.

In general, the training data can include signal evolution data in which each voxel is represented by one isochromat. A dictionary can be generated using the discrete form of the Bloch equations. The effect of RF pulses can be assumed to be instantaneous, and the RF-slice profile can be ignored for simplicity. B1 inhomogeneity can be explicitly included in the model as a scaling factor applied to the nominal FAs. In one non-limiting example, the simulated ranges can be: T1=[100:20:4000] ms, T2 and T2*=[5:5:30 32:2:130, 135: 5:200, 210:10:350] ms, and relative B1=[0.5:0.05:1.5]. The relative B1 is the scaling factor applied to the FA. The T1, T2 and T2* values can be chosen to specifically target the brain-tissue range, but in other clinical applications it will be appreciated that the T1, T2 and T2* values can be selected for different tissues. Overall a dictionary constructed in this manner will have approximately 180,000 entries, and in one example was generated in less than 15 minutes using a computer system having a single core 1.6 GHz processor.

One or more neural networks (or other suitable machine learning algorithms) are trained on the training data, as indicated at step 404. In general, the neural network can be trained by optimizing network parameters (e.g., weights, biases, or both) based on minimizing a loss function. As one non-limiting example, the loss function may be a mean squared error loss function.

Training a neural network may include initializing the neural network, such as by computing, estimating, or otherwise selecting initial network parameters (e.g., weights, biases, or both). Training data can then be input to the initialized neural network, generating output as estimated parameter maps. The quality of the output data can then be evaluated, such as by passing the output data to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

Figure 5:
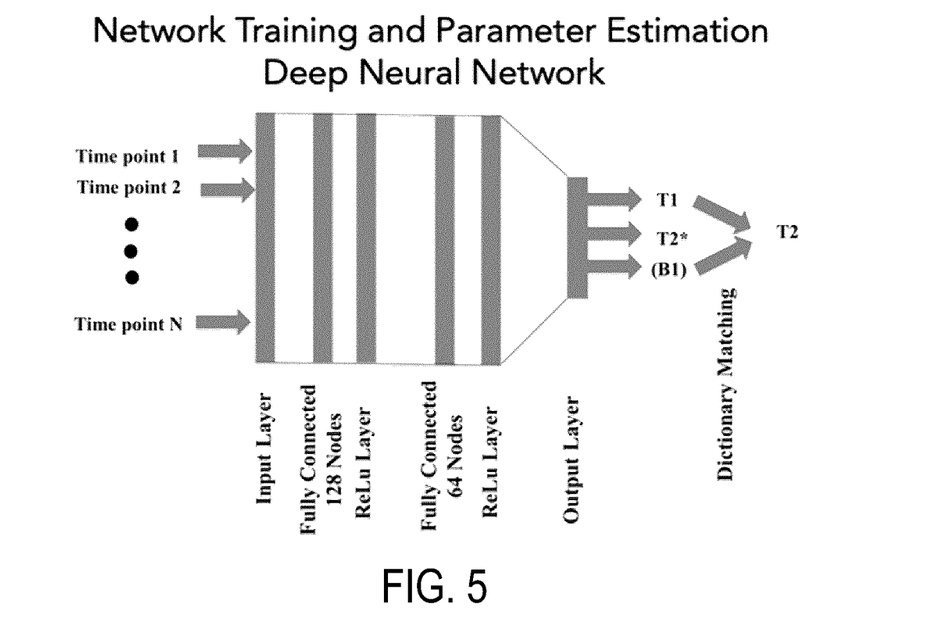
FIG. 5 is an example schematic of a deep neural network architecture that can be used to generate parameter maps from input magnetic resonance images. The network includes two fully connected hidden layers, with 128 nodes (neurons) and 64 nodes, respectively. The output layer produces T1 and T2* (as well as B1) estimates using the GE-EPI data. The T1 and B1 estimates then feed into the estimation of T2 based on the SE-EPI data.

An example of a deep neural network ("DNN") that can be trained according to some embodiments described in the present disclosure is shown in FIG. 5. This example DNN includes two hidden layers (containing 128 and 64 neurons, respectively) in which the input layer gets the fingerprint time series for each voxel and the output layer produces B1 corrected T1 and T2* estimates. The rectified linear unit (ReLU) function was used after each hidden layer. In other implementations, different activation functions could also be used. An Adam optimizer can be utilized to train the network using a constant learning rate of 0.001 (a configurable hyperparameter) and the minimum batch size of 1024. In one example, 100 Epochs were used for training, which took 10-15 minutes on a single computer running on CPU.

The one or more trained neural networks are then stored for later use, as indicated at step 406. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

Figure 6:
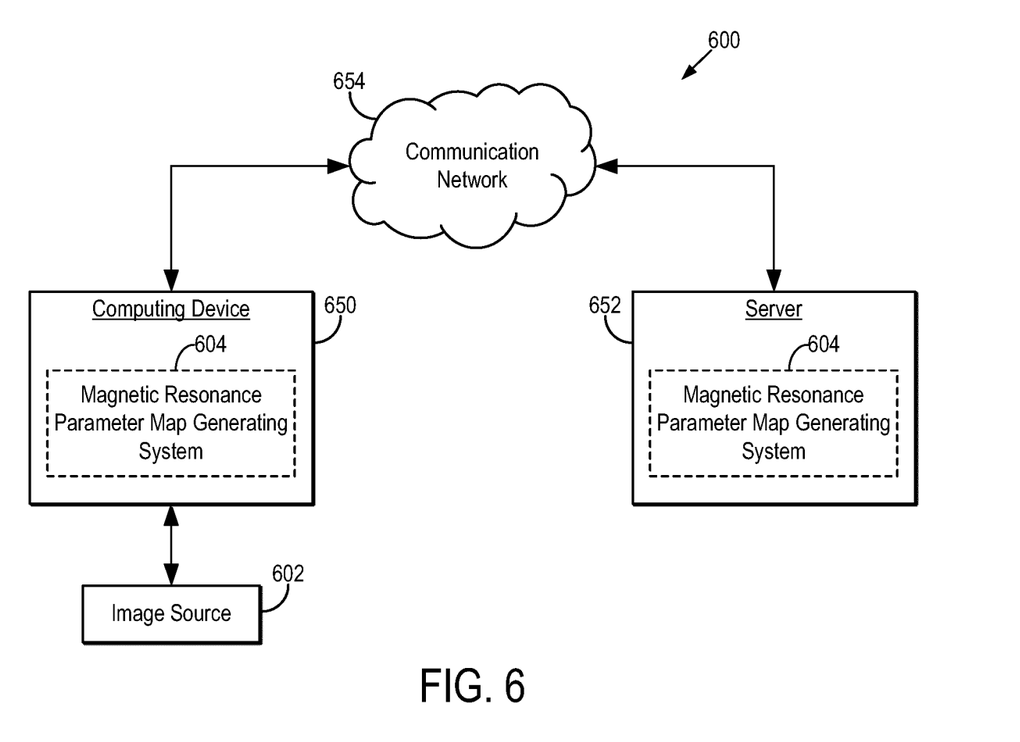
FIG. 6 is a block diagram of an example system for generating magnetic resonance parameter maps in accordance with some embodiments described in the present disclosure.

Referring now to FIG. 6, an example of a system 600 for generating parameter maps (e.g., T1, T2, T2*, and/or B1 maps) in accordance with some embodiments of the systems and methods described in the present disclosure is shown. As shown in FIG. 6, a computing device 650 can receive one or more types of data (e.g., magnetic resonance data, magnetic resonance images, parameter maps, training fata) from image source 602, which may be a magnetic resonance image source. In some embodiments, computing device 650 can execute at least a portion of a magnetic resonance parameter map generating system 604 to generate parameter maps (e.g., T1 maps, T2 maps, T2* maps, and/or B1 maps) from data received from the image source 602.

Additionally or alternatively, in some embodiments, the computing device 650 can communicate information about data received from the image source 602 to a server 652 over a communication network 654, which can execute at least a portion of the magnetic resonance parameter map generating system 604. In such embodiments, the server 652 can return information to the computing device 650 (and/or any other suitable computing device) indicative of an output of the magnetic resonance parameter map generating system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as an MRI system, another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
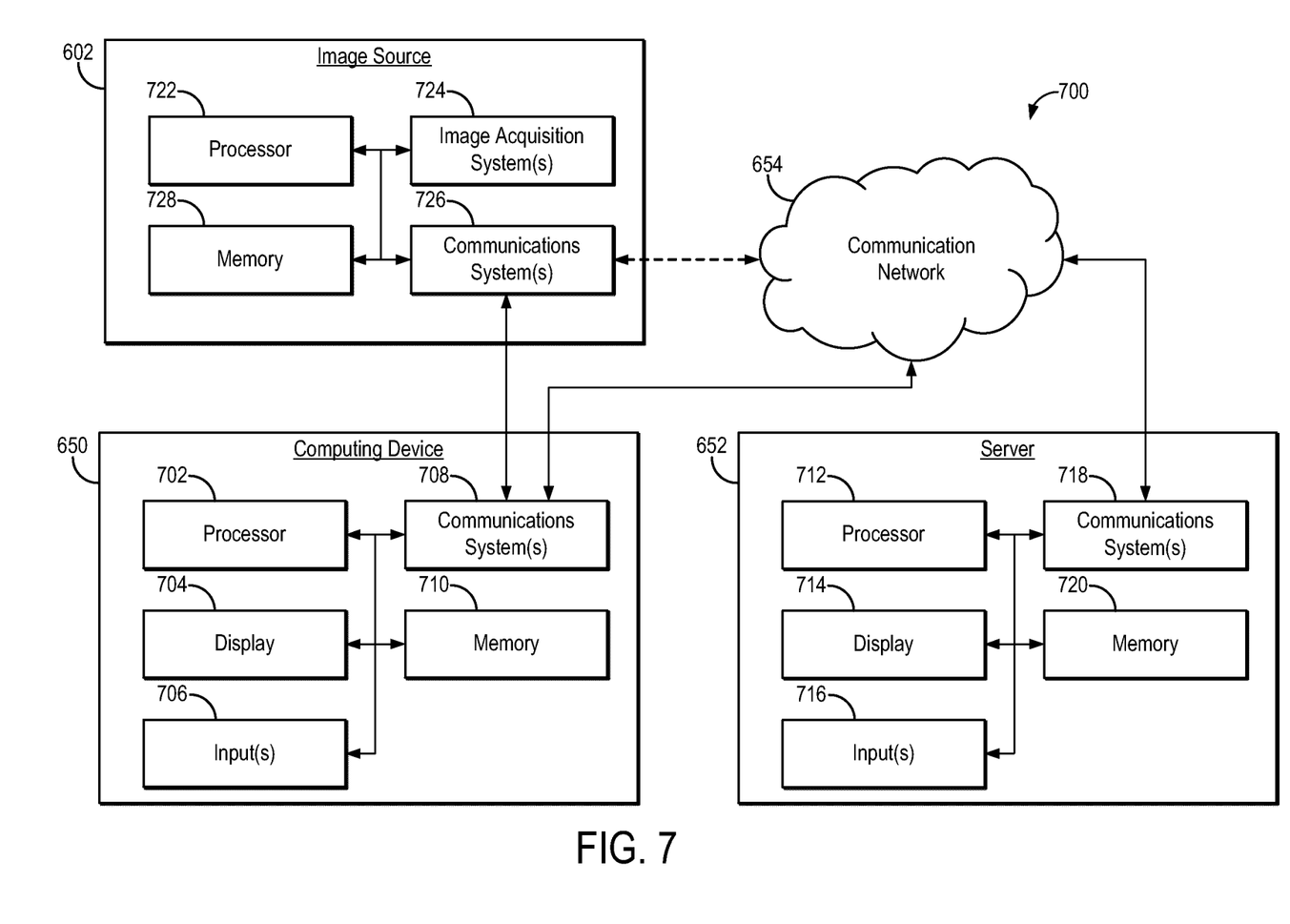
FIG. 7 is a block diagram of example components that can implement the system of FIG. 6.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include an MRI system. Additionally or alternatively, in some embodiments, one or more image acquisition systems 724 can include any suitable hardware, firmware, and/or software for coupling to and/or controlling operations of an MRI system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 8:
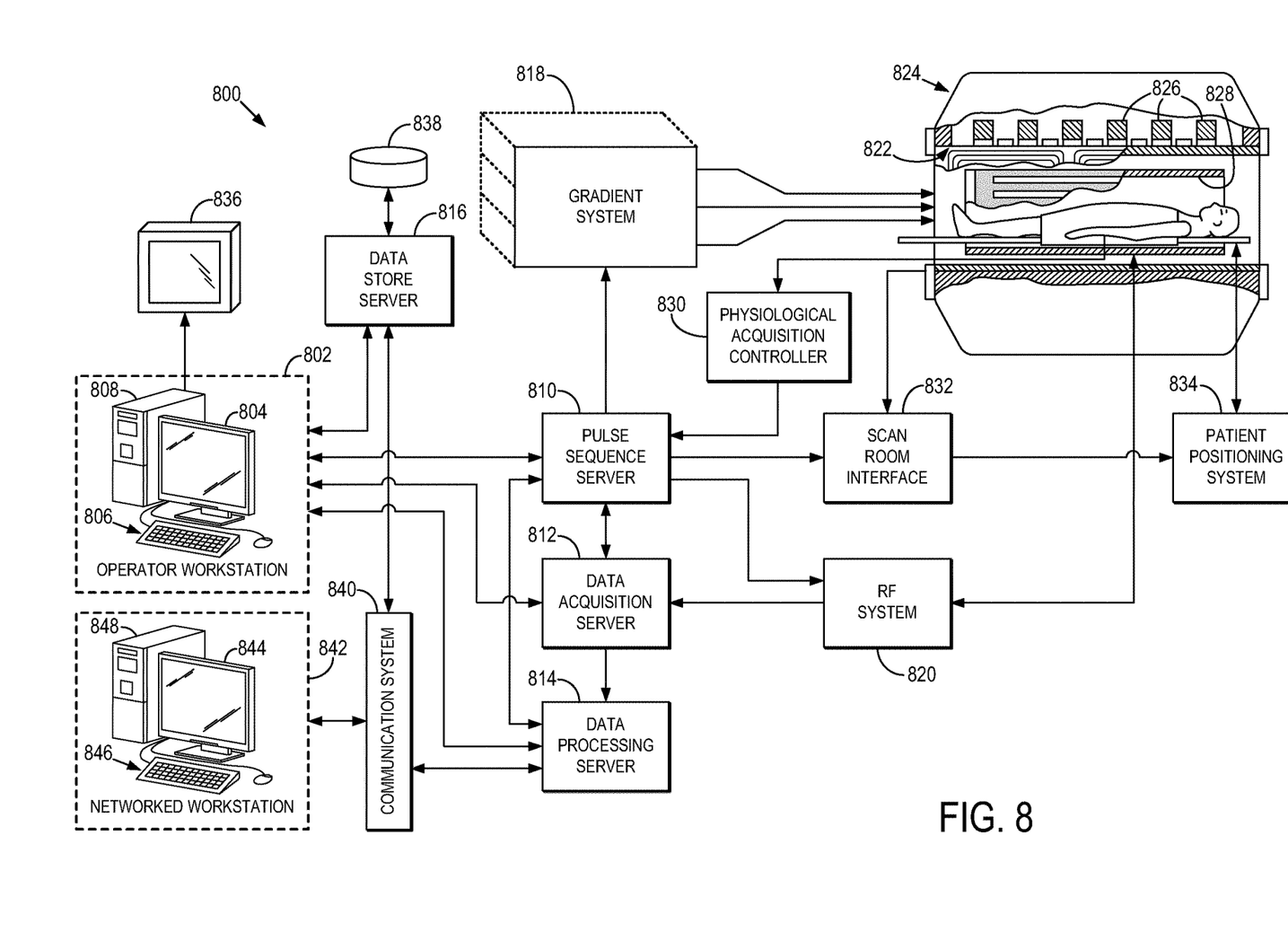
FIG. 8 is a block diagram of an example MRI system that can implement the methods described in the present disclosure.

Referring particularly now to FIG. 8, an example of an MRI system 800 that can implement the methods described here is illustrated. The MRI system 800 includes an operator workstation 802 that may include a display 804, one or more input devices 806 (e.g., a keyboard, a mouse), and a processor 808. The processor 808 may include a commercially available programmable machine running a commercially available operating system. The operator workstation 802 provides an operator interface that facilitates entering scan parameters into the MRI system 800. The operator workstation 802 may be coupled to different servers, including, for example, a pulse sequence server 810, a data acquisition server 812, a data processing server 814, and a data store server 816. The operator workstation 802 and the servers 810, 812, 814, and 816 may be connected via a communication system 840, which may include wired or wireless network connections.

The pulse sequence server 810 functions in response to instructions provided by the operator workstation 802 to operate a gradient system 818 and a radiofrequency ("RF") system 820. Gradient waveforms for performing a prescribed scan are produced and applied to the gradient system 818, which then excites gradient coils in an assembly 822 to produce the magnetic field gradients $G_x$, $G_y$, and $G_z$ that are used for spatially encoding magnetic resonance signals. The gradient coil assembly 822 forms part of a magnet assembly 824 that includes a polarizing magnet 826 and a whole-body RF coil 828.

RF waveforms are applied by the RF system 820 to the RF coil 828, or a separate local coil to perform the prescribed magnetic resonance pulse sequence. Responsive magnetic resonance signals detected by the RF coil 828, or a separate local coil, are received by the RF system 820. The responsive magnetic resonance signals may be amplified, demodulated, filtered, and digitized under direction of commands produced by the pulse sequence server 810. The RF system 820 includes an RF transmitter for producing a wide variety of RF pulses used in MRI pulse sequences. The RF transmitter is responsive to the prescribed scan and direction from the pulse sequence server 810 to produce RF pulses of the desired frequency, phase, and pulse amplitude waveform. The generated RF pulses may be applied to the whole-body RF coil 828 or to one or more local coils or coil arrays.

The RF system 820 also includes one or more RF receiver channels. An RF receiver channel includes an RF preamplifier that amplifies the magnetic resonance signal received by the coil 828 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (3);$$

and the phase of the received magnetic resonance signal may also be determined according to the following relationship:

$$\varphi = \tan^{-1}\left(\frac{Q}{I}\right). \qquad (4)$$

The pulse sequence server 810 may receive patient data from a physiological acquisition controller 830. By way of example, the physiological acquisition controller 830 may receive signals from a number of different sensors connected to the patient, including electrocardiograph ("ECG") signals from electrodes, or respiratory signals from a respiratory bellows or other respiratory monitoring devices. These signals may be used by the pulse sequence server 810 to synchronize, or "gate," the performance of the scan with the subject's heart beat or respiration.

The pulse sequence server 810 may also connect to a scan room interface circuit 832 that receives signals from various sensors associated with the condition of the patient and the magnet system. Through the scan room interface circuit 832, a patient positioning system 834 can receive commands to move the patient to desired positions during the scan.

The digitized magnetic resonance signal samples produced by the RF system 820 are received by the data acquisition server 812. The data acquisition server 812 operates in response to instructions downloaded from the operator workstation 802 to receive the real-time magnetic resonance data and provide buffer storage, so that data is not lost by data overrun. In some scans, the data acquisition server 812 passes the acquired magnetic resonance data to the data processor server 814. In scans that require information derived from acquired magnetic resonance data to control the further performance of the scan, the data acquisition server 812 may be programmed to produce such information and convey it to the pulse sequence server 810. For example, during pre-scans, magnetic resonance data may be acquired and used to calibrate the pulse sequence performed by the pulse sequence server 810. As another example, navigator signals may be acquired and used to adjust the operating parameters of the RF system 820 or the gradient system 818, or to control the view order in which k-space is sampled. In still another example, the data acquisition server 812 may also process magnetic resonance signals used to detect the arrival of a contrast agent in a magnetic resonance angiography ("MRA") scan. For example, the data acquisition server 812 may acquire magnetic resonance data and processes it in real-time to produce information that is used to control the scan.

The data processing server 814 receives magnetic resonance data from the data acquisition server 812 and processes the magnetic resonance data in accordance with instructions provided by the operator workstation 802. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 814 are conveyed back to the operator workstation 802 for storage. Real-time images may be stored in a data base memory cache, from which they may be output to operator display 802 or a display 836. Batch mode images or selected real time images may be stored in a host database on disc storage 838. When such images have been reconstructed and transferred to storage, the data processing server 814 may notify the data store server 816 on the operator workstation 802. The operator workstation 802 may be used by an operator to archive the images, produce films, or send the images via a network to other facilities.

The MRI system 800 may also include one or more networked workstations 842. For example, a networked workstation 842 may include a display 844, one or more input devices 846 (e.g., a keyboard, a mouse), and a processor 848. The networked workstation 842 may be located within the same facility as the operator workstation 802, or in a different facility, such as a different healthcare institution or clinic.

The networked workstation 842 may gain remote access to the data processing server 814 or data store server 816 via the communication system 840. Accordingly, multiple networked workstations 842 may have access to the data processing server 814 and the data store server 816. In this manner, magnetic resonance data, reconstructed images, or other data may be exchanged between the data processing server 814 or the data store server 816 and the networked workstations 842, such that the data or images may be remotely processed by a networked workstation 842.

The present disclosure has described one or more preferred embodiments, and it should be appreciated that many equivalents, alternatives, variations, and modifications, aside from those expressly stated, are possible and within the scope of the invention.

The invention claimed is:

1. A method for generating T1, T2, and T2* parameter maps from data acquired with a magnetic resonance imaging (MRI) system, the method comprising:

(a) acquiring magnetic resonance data from a subject by operating an MRI system to acquire the magnetic resonance data in a series of variable sequence blocks to cause one or more resonant species in the subject to simultaneously produce individual magnetic resonance signals, wherein at least one member of the series of variable sequence blocks differs from at least one other member of the series of variable sequence blocks in at least one sequence block parameter, wherein the series of sequence blocks includes a first segment comprising a first plurality of variable sequence blocks in which data are acquired by sampling gradient echoes and a second segment comprising a second plurality of variable sequence blocks in which data are acquired by sampling spin echoes;

wherein the magnetic resonance data comprises first magnetic resonance data acquired during the first segment and second magnetic resonance data acquired during the second segment;

(b) generating a first series of parameter maps by estimating T1 and T2* values with a computer system by comparing the first magnetic resonance data to a dictionary of signal evolutions, the first series of parameter maps depicting spatial distributions of T1 and T2* values; and (c) generating a second series of parameter maps by estimating T2 values with the computer system by comparing the second magnetic resonance data to the dictionary of signal evolutions while constraining T1 values with those estimated in step (b), wherein the second series of parameter maps depict spatial distributions of T2 values.

2. The method of claim 1, wherein each of the variable sequence blocks in the first segment and the second segment include an echo planar imaging (EPI) readout.

3. The method of claim 1, wherein the first segment comprises a larger number of sequence blocks than the second segment.

4. The method of claim 1, wherein the series of variable sequence blocks include multiband radio frequency (RF) excitation pulses in order to implement a simultaneous multislice (SMS) acquisition.

5. The method of claim 4, wherein each of the variable sequence blocks in the first segment and the second segment include an echo planar imaging (EPI) readout.

6. The method of claim 5, wherein the SMS acquisition comprises a blipped-CAIPI acquisition.

7. The method of claim 1, wherein generating the first series of parameter maps also includes estimating B1 values with the computer system by comparing the first magnetic resonance data to the dictionary of signal evolutions, such that the first series of parameter maps depict spatial distributions of T1, T2* and B1 values.

8. The method of claim 7, wherein generating the second series of parameter maps comprises estimating T2 values with the computer system by comparing the second magnetic resonance data to the dictionary of signal evolutions while constraining both T1 and B1 values with the estimated T1 and B1 values in the first series of parameter maps.

9. The method of claim 1, wherein generating the first series of parameter maps comprises:

accessing a trained neural network with the computer system, wherein the trained neural network has been trained based in part on the dictionary of signal evolutions;

inputting the first magnetic resonance data to the trained neural network, generating output as the first series of parameter maps.

10. The method of claim 9, wherein the trained neural network comprises a deep neural network.

11. The method of claim 9, wherein generating the second series of parameter maps comprises:

accessing another trained neural network with the computer system, wherein the trained neural network has been trained based in part on the dictionary of signal evolutions;

inputting the second magnetic resonance data and the first series of parameter maps to the trained neural network, generating output as the second series of parameter maps.

12. The method of claim 11, wherein the another trained neural network comprises another deep neural network.

13. The method of claim 1, wherein the first magnetic resonance data and the second magnetic resonance data each comprise magnetic resonance images.

14. The method of claim 1, further comprising displaying one or more of the first series of parameter maps or second series of parameter maps to a user.

* * * * *